United States Patent
Shin et al.

(10) Patent No.: US 10,279,076 B2
(45) Date of Patent: *May 7, 2019

(54) COMPOSITION FOR MAINTAINING EFFICACY OF FILLER

(71) Applicant: AMOREPACIFIC CORPORATION, Seoul (KR)

(72) Inventors: Hyun Jung Shin, Yongin-si (KR); Jin Kyu Choi, Yongin-si (KR); Byung Gyu Kim, Yongin-si (KR); Dae Bang Seo, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/127,399

(22) PCT Filed: Mar. 10, 2015

(86) PCT No.: PCT/KR2015/002294
§ 371 (c)(1),
(2) Date: Sep. 19, 2016

(87) PCT Pub. No.: WO2015/141978
PCT Pub. Date: Sep. 24, 2015

(65) Prior Publication Data
US 2017/0136146 A1    May 18, 2017

(30) Foreign Application Priority Data
Mar. 20, 2014 (KR) .......... 10-2014-0032945
Mar. 4, 2015 (KR) .......... 10-2015-0030409

(51) Int. Cl.
A61L 27/24   (2006.01)
A61L 27/20   (2006.01)
A61L 27/50   (2006.01)
A61L 27/52   (2006.01)

(52) U.S. Cl.
CPC .......... *A61L 27/24* (2013.01); *A61L 27/20* (2013.01); *A61L 27/505* (2013.01); *A61L 27/52* (2013.01); *A61L 2400/06* (2013.01)

(58) Field of Classification Search
CPC ...... A61L 2400/06; A61L 27/20; A61L 27/24; A61L 27/505
See application file for complete search history.

(56) References Cited

U.S. PATENT DOCUMENTS

| 7,678,768 B2 | 3/2010 | Purpura et al. |
| 2005/0147679 A1* | 7/2005 | Petito ............... A61K 38/39 424/484 |
| 2011/0160137 A1 | 6/2011 | Kim et al. |
| 2012/0164116 A1* | 6/2012 | Van Epps ........... A61L 27/3839 424/93.7 |

FOREIGN PATENT DOCUMENTS

| KR | WO 2007/106457 | 9/2007 |
| KR | 10-2008-0109774 A | 12/2008 |
| KR | 10-2010-0025500 A | 3/2010 |
| KR | 10-2010-0101715 A | 9/2010 |
| KR | 10-1082895 B1 | 11/2011 |
| KR | 10-1238730 B1 | 3/2013 |

OTHER PUBLICATIONS

Yasuo Sakai, Google English Translation of JP2003137807A, Collagen-producing promoter, cosmetic, food and pharmaceutical containing the same and external preparation for preventing or improving dermatosis, published May 14, 2003.*
Takahiro Hongo, Google English Translation JP2004123637A , Hyaluronic acid production promoter , Published Apr. 22, 2004.*
International Search Report for PCT/KR2015/002294 (dated Jun. 16, 2015).
Written Opinion for PCT/KR2015/002294 (dated Jun. 16, 2015).
Steed, "Modifying the Wound Healing Response With Exogenous Growth Factors," *Clinics in Plastic Surgery*, 25(3):397-405 (Jul. 1998).

* cited by examiner

*Primary Examiner* — Rachael E Bredefeld
*Assistant Examiner* — Erinne R Dabkowski
(74) *Attorney, Agent, or Firm* — Merchant & Gould P.C.

(57) ABSTRACT

The present invention relates to a parenteral composition for maintaining the efficacy of a filler for a long time, containing a collagen hydrolysate as an active ingredient. The composition, according to the present invention, can maintain the efficacy of a hyaluronic acid filler for a longer time, thereby enabling the effect thereof to be maintained irrespective of a smaller frequency of filler operations, and thus there is an advantage of also reducing skin irritation. In addition, there is an advantage of enabling an immediate effect since an administration method is simple as a parenteral administration and enables direct penetration into the skin.

7 Claims, 1 Drawing Sheet

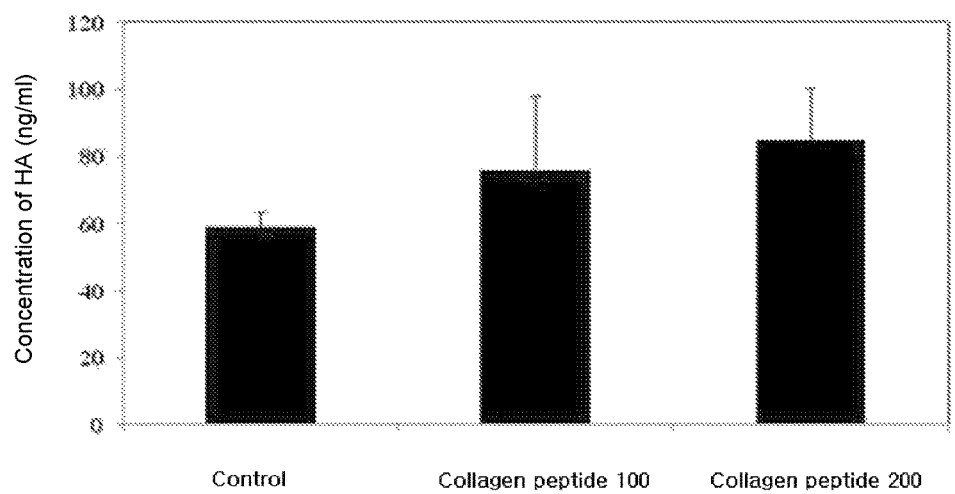

COMPOSITION FOR MAINTAINING EFFICACY OF FILLER

This application is a U.S. National Stage Application under 35 U.S.C. § 371 of International Patent Application No. PCT/KR2015/002294 filed 10 Mar. 2015, which claims the benefit of priority to Korean Patent Application No. 10-2015-0030409 filed 4 Mar. 2015, and also claims the benefit of priority to Korean Patent Application No. 10-2014-0032945 filed 20 Mar. 2014, the disclosures of all of which are hereby incorporated by reference in their entireties. The International Application was published in Korean on 24 Sep. 2015 as WO 2015/141978.

TECHNICAL FIELD

The present disclosure relates to a parenteral composition which maintains the effect of a filler for a long period of time.

BACKGROUND

A material implanted into living tissues should be non-toxic and, after the desired function has been achieved, degraded by metabolic activities and cleared out of the body. Recently, implantation of specific substances into the skin tissue for cosmetic purposes is increasing rapidly. Hyaluronic acid, which is commonly used for this purpose, is known to be metabolized and cleared out of the body within a few days after insertion or implantation regardless of the concentration or the type of the composition. To maintain the desired cosmetic effect for a long period of time, it is necessary to overcome the short period of metabolism of hyaluronic acid in the human body. Therefore, needs on the development of a new filler material that can be maintained for months or longer are increasing.

REFERENCES OF RELATED ART

Non-Patent Document (Non-patent document 1) Steed, D. L. et al., *Clin. Plast. Surg.* 25, 397, 1998.

DISCLOSURE

Technical Problem

The present disclosure is directed to providing a composition that can maintain the effect of a hyaluronic acid filler for a long period of time after a filler treatment thereof.

Technical Solution

In an aspect, the present disclosure provides a parenteral composition for maintaining the effect of a hyaluronic acid filler, a parenteral composition for promoting the synthesis of hyaluronic acid and a parenteral composition for inhibiting the activity of hyaluronidase, which contain collagen hydrolysate as an active ingredient.

In another aspect, the present disclosure provides a kit for a filler treatment, which contains a filler composition comprising a hyaluronic acid and collagen hydrolysate as active ingredients.

Advantageous Effects

Since a composition according to the present disclosure can promote the synthesis of hyaluronic acid and inhibit the activity of hyaluronidase, it is useful in maintaining the effect of a hyaluronic acid filler for a longer period of time. As a result, the effect of the filler can be maintained even with a smaller number of filler treatments and skin irritation can also be reduced. In addition, since the composition can be directly injected into the skin by simple parenteral administration, an immediate effect can be achieved.

BRIEF DESCRIPTION OF DRAWINGS

FIG. 1 shows increased level of hyaluronic acid synthesis as a result of treatment with collagen peptide.

BEST MODE

In an aspect, the present disclosure relates to a parenteral composition for maintaining the effect of a hyaluronic acid filler, which contains collagen hydrolysate as an active ingredient.

Collagen is one of scleroproteins and contains a small amount of sugar. It is the main component of connective tissue and makes up about 30 wt % of the whole-body protein content in mammals. Collagen is present in the form of fibrils in the dermis, cartilage, etc. of animals and multiple collagen fibrils form into collagen fibers. The basic unit constituting the fiber is tropocollagen with a molecular weight of about 300,000, which is approximately 280 nm long and 1.5 nm in diameter.

The composition according to the present disclosure may maintain a hyaluronic acid filler more naturally for a longer period of time after being injected into the skin.

In another aspect, the present disclosure relates to a parenteral composition for promoting the synthesis of hyaluronic acid, which contains collagen hydrolysate as an active ingredient.

The collagen hydrolysate may promote the synthesis of hyaluronic acid and enhance the activity or quantity of enzymes or proteins involved in the synthesis of hyaluronic acid.

In another aspect, the present disclosure relates to a parenteral composition for inhibiting the activity of hyaluronidase, which contains collagen hydrolysate as an active ingredient.

The collagen hydrolysate may inhibit the degradation of hyaluronic acid by inhibiting the activity of hyaluronidase or reducing its quantity. Accordingly, the synthesis of hyaluronic acid may be promoted and the effect of the filler may be maintained for a long period of time.

In this aspect, the collagen hydrolysate may include collagen peptide, specifically collagen tripeptide.

In the present disclosure, the collagen peptide is not particularly limited as long as it is a peptide having a molecular weight of 500-1,000 Da wherein amino acids are linked by peptide bonding.

In the present disclosure, the collagen hydrolysate refers to a substance obtained from hydrolysis of collagen, which includes a peptide having an average molecular weight of 500-5,000 Da.

And, in the composition according to the present disclosure, the collagen hydrolysate may contain the collagen tripeptide in an amount of 10 wt % or more based on the total weight of the collagen hydrolysate. However, without being limited thereto, the content may be 7% or more, 9% or more, 11% or more, 13% or more, 15% or more, 17% or more or 19% or more.

In the present disclosure, the 'hyaluronic acid filler' may mean a filler containing hyaluronic acid (HA) as a main ingredient. The hyaluronic acid is one of complex polysaccharides composed of amino acids and uronic acids, and is a polymer compound consisting of N-acetylglucosamine and glucuronic acid. The filler may mean a substitute material directly injected or inserted into the skin to fill wrinkles, depressed scars, etc. The filler may be used for various purposes without limitation, including alleviation of skin wrinkles, replenishment of moisture, or the like. The filler may be injected into the any part of the body, including, specifically, face, neck, etc.

In the present disclosure, 'to maintain the effect of a filler' means that the injected filler is degraded more slowly or that the content of hyaluronic acid which is the main ingredient of the filler is increased by promoting the synthesis of hyaluronic acid in vivo.

The composition of the present disclosure is useful since it can maintain the effect of a filler, including but not being limited to alleviation of skin wrinkles, replenishment of moisture, etc., for a long period of time. Specifically, it is advantageous in terms of skin irritation and economy since the filler injection cycle can be increased.

In the present disclosure, 'parenteral' means any non-oral route of administration. Specifically, it can mean transdermal, topical or subcutaneous administration, although not being limited thereto.

The composition according to the present disclosure may contain 0.01-50 wt % of collagen hydrolysate based on the total weight of the composition. Within this range, the composition may maintain the effect of the hyaluronic acid filler for a long period of time by promoting the synthesis of hyaluronic acid. In this aspect, the composition according to the present disclosure may contain the collagen hydrolysate in an amount of 0.05-48 wt % based on the total weight of the composition, 0.1-46 wt % based on the total weight of the composition, 0.5-44 wt % based on the total weight of the composition, 1-42 wt % based on the total weight of the composition or 5-40 wt % based on the total weight of the composition.

Specifically, the collagen tripeptide may include the collagen tripeptide Glycine (Gly)-X-Y, wherein X and Y may be any naturally occurring amino acids. The X and the Y may be the same or different amino acids.

In the composition according to the present disclosure, the collagen hydrolysate may contain the collagen tripeptide Gly-X-Y.

In the composition according to the present disclosure, the X and the Y may be the same or different amino acids and the amino may be selected from a group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp) and proline (Pro).

Specifically, the collagen tripeptide may include glycine-proline-hydroxyproline, with the X being proline and the Y being hydroxyproline, although not being limited thereto.

The composition according to the present disclosure may be a pharmaceutical composition.

The pharmaceutical composition according to the present disclosure may be prepared into a solid, semisolid or liquid formulation for parenteral administration by adding a commonly used inorganic or organic carrier to the active ingredient.

The formulation for parenteral administration may be injection, drop, ointment, lotion, spray, suspension, emulsion, suppository, etc. The active ingredient of the present disclosure may be easily prepared into the desired formulation according to a commonly employed method by using a surfactant, an excipient, a colorant, a flavoring agent, a preservative, a stabilizer, a buffer, a suspending agent or other commonly used adjuvants.

The pharmaceutical composition according to the present disclosure may be administered parenterally, e.g., topically, transdermally, subcutaneously, etc.

The dosage of the active ingredient will vary depending on the age, sex and body weight of a subject, particular disease or pathological condition to be treated and severity thereof, administration route or the discretion of a diagnoser. Determination of the dosage considering these factors is in the level of those skilled in the art. A general dosage is 0.001-2,000 mg/kg/day, more specifically 0.5-1,500 mg/kg/day.

The pharmaceutical composition of the present disclosure may be used to remove or alleviate scars or to reconstitute or restore damaged or destroyed skin tissues. The scar or the damaged/destroyed skin tissue may mean the marks left on the skin for various causes. For example, they may mean depressions on the skin. The causes may include, for example, burn, wound, etc.

The composition according to the present disclosure may be a cosmetic composition.

The cosmetic composition according to the present disclosure may be prepared into any formulation suitable for topical application. For example, it may be formulated into solution, suspension, emulsion, paste, gel, cream, lotion, powder, soap, surfactant-containing cleanser, oil, powder foundation, emulsion foundation, wax foundation, spray, etc. Specifically, it may be formulated into oil-in-water emulsion, water-in-oil emulsion, solid, powder, foam, softening lotion, astringent lotion, nourishing lotion, eye cream, nourishing cream, massage cream, cleansing cream, cleansing foam, cleansing water, essence or pack. These formulations can be prepared by the methods commonly employed in the art.

The cosmetic composition according to the present disclosure may contain, in addition to the active ingredient, other ingredients that provide a synergic effect within the range not negatively affecting the effect of the active ingredient. In addition, the cosmetic composition according to the present disclosure may further contain a humectant, an emollient, a UV absorbent, a preservative, a sterilizer, an antioxidant, a pH control agent, an organic or inorganic pigment, a fragrance, a cooling agent or an antiperspirant. The amount of these ingredients may be easily determined by those skilled in the art within the range not negatively affecting the purpose and effect of the present disclosure. The amount may be 0.01-5 wt %, specifically 0.01-3 wt, based on the total weight of the composition.

In another aspect, the present disclosure relates to a kit for a filler treatment, containing: a filler composition comprising a hyaluronic acid; and a composition containing collagen hydrolysate as active ingredients.

The filler composition may be an injection.

The kit according to the present disclosure may further contain a written instruction which instructs that the filler composition is administered by injection and the composition containing collagen hydrolysate is transdermally administered.

The filler may be either applied on the skin so that it can be absorbed into the skin or inserted into the skin. For example, the administration of the filler composition (hereinafter, filler treatment) may be administration of the composition containing the hyaluronic acid filler by injection and the number of injection is not limited.

The composition containing collagen hydrolysate according to the present disclosure may be used prior to the filler treatment.

In this aspect, the written instruction may instruct that the filler composition is administered by injection after transdermal administration of the composition containing collagen hydrolysate for 1-50 days.

For example, the filler injection may be performed after transdermal administration of the composition containing collagen hydrolysate for 1-50 days, 10-50 days, 10-40 days, 10-30 days, 10-20 days, 20-50 days, 20-40 days, 20-30 days, 25-45 das, 25-35 days, 30-50 days or 30-40 days.

Also, the composition containing collagen hydrolysate may be used simultaneously with, after or before and after the filler treatment.

Specifically, it may be transdermally administered 1-20 days, 1-15 days, 1-10 days, 1-5 days, 1-4 days, 1-3 days or 1-2 days after the filler injection. Alternatively, the collagen hydrolysate may be transdermally administered within 24 hours, 20 hours, 15 hours, 10 hours, 5 hours, 3 hours or 1 hour after the filler treatment.

The collagen hydrolysate may prolong the duration of the effect of the filler.

Hereinafter, the present disclosure will be described in detail through examples. However, the following examples are for illustrative purposes only and it will be apparent to those of ordinary skill in the art that the scope of the present disclosure is not limited by the examples.

[Preparation Example 1] Preparation of Collagen Peptide

Collagen peptide used as the active ingredient in the present disclosure, purchased from Jellice (HATC, Jellice Co., Japan), contains 15% or more of a tripeptide such as glycine-proline-hydroxyproline.

[Test Example 1] Ability of Promoting Synthesis of Hyaluronic Acid (HA) in Keratinocytes Human-derived HaCaT keratinocytes (Dr N. E. Fusenig, Deutsches Krebsforschungszentrum, Heidelberg, Germany) were cultured in a DMEM medium containing 10% FBS under the condition of 37° C. and 5% $CO_2$. The cells were cultured on a 96-well plate. Upon reaching 80% confluence, the medium was replaced with an FBS-free medium and the cells were cultured for 24 hours. Subsequently, the cells were treated with the collagen peptide of Preparation Example 1, diluted 200-fold in PBS, with a final concentration of 100 ppm or 200 ppm and then cultured for 24 hours. 24 hours later, the medium was recovered and used for hyaluronic acid (HR) assay. The remaining cells were subjected to quantitative cell viability (CCK8) assay.

The CCK8 assay (Dojindo) and the hyaluronic acid assay (Echelon) were conducted according to the protocols of the kit manufacturers. The quantitated hyaluronic acid value was corrected by dividing with the cell viability value.

As a result, the collagen peptide-treated group showed 30-44% increased hyaluronic acid synthesis as compared to the untreated control group, as seen from FIG. 1. The promotion of the hyaluronic acid synthesis was proportional to the concentration of the collagen peptide. Accordingly, it was confirmed that the collagen peptide can promote the synthesis of hyaluronic acid in skin cells.

[Test Example 2] Ability of Inhibiting Activity of Hyaluronidase

The effect of inhibiting the activity of hyaluronidase was investigated to confirm whether the hydrolysis of hyaluronic acid which is the main ingredient of the filler is inhibited.

20 μL of collagen peptide was added to 50 μL of a 0.1 M hyaluronidase solution (7,900 units/mL), with a final concentration of 0.2, 0.4, 0.6, 0.8 or 1.0 mg/mL. After mixing with 200 μL of 12.5 mM $CaCl_2$ to activate the enzyme, incubation was performed in an aqueous solution at 37° C. for 20 minutes. For the control group, distilled water was added instead of the collagen peptide and incubation was performed for 20 minutes in an aqueous solution. After adding 250 μL of a 0.1 M hyaluronic acid solution (12 mg/5 mL) to the hyaluronidase solution activated with $Ca^{2+}$, incubation was performed again in an aqueous solution for 40 minutes. After the incubation, 100 μL of a 0.4 N NaOH solution and 100 μL of 0.4 M potassium tetraborate were added to the reaction mixture and then cooled after incubation in a boiling water bath for 3 minutes. After adding 3.28 mL of a dimethylaminobenzaldehyde solution (a mixture of 4 g of p-dimethylamino-benzaldehyde, 350 mL of 100% acetic acid and 50 mL of 10 N HCl) to the cooled reaction mixture and incubating in a water bath at 37° C. for 20 minutes, absorbance was measured at 585 nm.

As can be seen from Table 1, the collagen peptide exhibited superior effect of inhibiting the activity of hyaluronidase. The effect was dependent on the concentration of the collagen peptide.

TABLE 1

| | | | | | |
|---|---|---|---|---|---|
| Concentration of collagen peptide (mg/mL) | 0.2 | 0.4 | 0.6 | 0.8 | 1.0 |
| Inhibition of hyaluronidase activity (%) | 30.4 | 32.8 | 48.6 | 75.2 | 82.4 |

[Test Example 3] Ability of Maintaining Hyaluronic Acid Filler in Living Tissues A clinical test was conducted to investigate the effect of application of a collagen-containing cosmetic product on the duration of the effect of a hyaluronic acid filler.

Six women who require improvement of nasolabial folds were selected and divided into a control group and a test group. The number of member which belong to each group was 3 (n=3). Those in the test group applied a collagen-containing cosmetic product on the on the face for a month, whereas those in the control group did not apply the collagen-containing cosmetic product on the face. One month later, the hyaluronic acid filler was injected into both nasolabial folds one time and clinical evaluation was made 15 days, 1 month, 2 months and 3 months after the injection. The clinical evaluation was made by an expert based on visual inspection according to the 5-point wrinkle severity rating scale (WSRS). The result is shown in Table 2. In Table 2, the lower score means less discernible wrinkles.

TABLE 2

| | Control group | Test group |
|---|---|---|
| Before injection | 4.67 | 4.67 |
| 15 days later | 1.00 | 1.00 |
| 1 month later | 2.33 | 1.33 |

TABLE 2-continued

|  | Control group | Test group |
|---|---|---|
| 2 months later | 3.33 | 2.33 |
| 3 months later | 3.67 | 2.67 |

As can be seen from Table 2, the test group showed lower points than the control group after the filler injection. This confirms that the administration of the composition according to the present disclosure maintains the effect of the injected filler even after passage of time or slows the decrease of the effect.

In addition, the satisfaction of the subjects who participated in the test was investigated according to the global aesthetic improvement scale (GAIS). The result is shown in Table 3.

TABLE 3

|  | Control group | Test group |
|---|---|---|
| Very satisfied |  | n = 1 |
| Slightly satisfied |  | n = 2 |
| Average | n = 2 |  |
| Slightly dissatisfied | n = 1 |  |
| Very dissatisfied |  |  |

As can be seen from Table 3, the test group expressed satisfaction as the effect of the filler was maintained for a long period of time, whereas the control group showed satisfaction below average.

Hereinafter, the present disclosure will be described in detail through formulation examples. However, the following formulation examples are for illustrative purposes only and it will be apparent to those of ordinary skill in the art that the scope of the present disclosure is not limited by the formulation examples.

[Formulation Example 1] Softening Lotion (Skin Lotion)

TABLE 4

| Ingredients | Contents (wt %) |
|---|---|
| Collagen peptide of Preparation Example 1 | 0.1 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | Adequate |
| Purified water | Balance |

[Formulation Example 2] Nourishing Lotion (Milk Lotion)

TABLE 5

| Ingredients | Contents (wt %) |
|---|---|
| Collagen peptide of Preparation Example 1 | 0.5 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment and fragrance | Adequate |
| Purified water | Balance |

[Formulation Example 3] Nourishing Cream

TABLE 6

| Ingredients | Contents (wt %) |
|---|---|
| Collagen peptide of Preparation Example 1 | 1.0 |
| Glycerin | 3.0 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, pigment and fragrance | Adequate |
| Purified water | Balance |

[Formulation Example 4] Massage Cream

TABLE 7

| Ingredients | Contents (wt %) |
|---|---|
| Collagen peptide of Preparation Example 1 | 1.5 |
| Glycerin | 8.0 |
| Butylene glycol | 4.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Preservative, pigment and fragrance | Adequate |
| Purified water | Balance |

[Formulation Example 5] Pack

TABLE 8

| Ingredients | Contents (wt %) |
| --- | --- |
| Collagen peptide of Preparation Example 1 | 0.1 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol preservative | 6.0 |
| Preservative, pigment and fragrance | Adequate |
| Purified water | Balance |

[Formulation Example 6] Ointment

TABLE 9

| Ingredients | Contents (wt %) |
| --- | --- |
| Collagen peptide of Preparation Example 1 | 0.1 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, pigment and fragrance | Adequate |
| Purified water | Balance |

[Formulation Example 7] Injection

| Collagen peptide of Preparation Example 1 | 200 mg |
| --- | --- |
| Sterile distilled water for injection | Adequate |
| pH control agent | Adequate |

An injection was prepared with the above ingredients per ampoule (2 mL) according to a commonly employed injection preparation method.

While some aspects of the present disclosure have been described in detail, it will be obvious to those skilled in the art that the detailed description is provided only as specific embodiments and the scope of the present disclosure is not limited thereby. Accordingly, the substantial scope of the present disclosure will be determined by the appended claims and their equivalents.

The invention claimed is:

1. A method for maintaining a filling effect of a hyaluronic acid filler comprising parenterally administering an effective amount of collagen hydrolysate to a subject in need thereof, wherein the collagen hydrolysate maintains the filling effect of the hyaluronic acid filler, wherein the collagen hydrolysate is applied on the skin of the subject in need thereof, and wherein the hyaluronic acid filler is administered after the collagen hydrolysate is applied, and wherein the collagen hydrolysate inhibits an activity of hyaluronidase and wherein the collagen hydrolysate comprises a concentration of collagen peptide of 0.1-1.5 mg/mL.

2. The method according to claim 1, wherein the collagen hydrolysate comprises a collagen tripeptide.

3. The method according to claim 1, wherein the collagen hydrolysate is administered in a form of a parenteral composition and the composition comprises 0.01-50 wt % of collagen hydrolysate based on the total weight of the composition.

4. The method according to claim 2, wherein the collagen tripeptide comprises Glycine (Gly)-X-Y, wherein the X and the Y are amino acids.

5. The method according to claim 4, wherein the X and the Y are the same or different, and wherein the amino acids are selected from a group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp) and proline (Pro).

6. The method according to claim 4, wherein the X and the Y are the same or different, and wherein the amino acids are selected from proline and hydroxyproline.

7. The method according to claim 4, wherein the X is proline and the Y is hydroxyproline.

\* \* \* \* \*